US00PP09195P

United States Patent [19]

Enthoven

[11] Patent Number: Plant 9,195

[45] Date of Patent: Jul. 11, 1995

[54] GERANIUM PLANT NAMED 'MERISWEET'

[75] Inventor: Adrianus W. M. Enthoven, Wateringen, Netherlands

[73] Assignee: Enthoven Breeding B.V., Wateringen, Netherlands

[21] Appl. No.: 217,123

[22] Filed: Mar. 24, 1994

[51] Int. Cl.[6] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Foley & Lardner

[57] ABSTRACT

A new and distinct cultivar of geranium named Merisweet particularly characterized by the combined features of semi-double flowers that are pale lilac with a dark center on the upper face and white on the lower face, elliptic flower buds, early and uniform flowering, inflorescences with big open flowers; relatively long flower pedicels which are green in color; short and thick and flower stems that extend above the plant; compact growth habit; green foliage with a light zone on the upper side, and leaf margins that are double crenated and slightly wavy.

3 Drawing Sheets

The present invention comprises a new and distinct cultivar of geranium, botanically known as *Pelargonium zonale,* and hereinafter referred to by the cultivar name Merisweet.

Merisweet is a product of planned breeding program which had the objective of creating new geranium cultivars with semi-double flower form, compact habit, fast rooting, good tolerance to Botrytis, superior weather resistance and little need for growth regulators.

Merisweet was originated from a hybridization made by the inventor in a controlled breeding program in Wateringen, The Netherlands in 1986. The female parent was proprietary Enthoven seedling Nr. 23, characterized by it compact growth. The male parent of Merisweet was proprietary Enthoven seedling Nr. 36.04, characterized by its weather resistance.

Merisweet was discovered and selected as one flowering plant within the progeny of the stated cross by Adrianus W. M. Enthoven in June 1987 in a controlled environment in Wateringen, The Netherlands.

The first act of asexual reproduction of Merisweet was accomplished when vegetative cuttings were taken from the initial selection in August 1987 in a controlled environment in Wateringen, The Netherlands under the supervision of Adrianus W. M. Enthoven.

Horticultural examination of selected units initiated in the spring and summer of 1988, and continuing thereafter, has demonstrated that the combination of characteristics as herein disclosed for Merisweet are firmly fixed and are retained through successive generations of asexual reproduction.

Merisweet has not been observed under all possible environmental conditions. The phenotype may vary with variations in environment such as temperature, light intensity and day length, without, however, any variation in genotype.

The following measurements, and comparison describe plants grown in Wateringen, The Netherlands under greenhouse and outdoors conditions which approximate those generally used in commercial practice.

The following traits have been repeatedly observed and are determined to be basic characteristics of Merisweet, which in combination distinguish this geranium as a new and distinct cultivar:

1. The plant has a compact growth habit and grows rather wide.
2. The foliage is green (R.H.S. 138A) with a light and very weak (R.H.S. 137C) zone on the upperside.
3. The leaf margins are double crenated and slightly wavy.
4. The leaf stalks are green, short and sturdy.
5. The flower stalks are short and thick and extend above the plant.
6. The inflorescence is large with many open flowers.
7. The flower pedicels are long and green in color.
8. The many flower buds are elliptic in shape.
9. The flowers are semi-double and bicolor with a pale lilac upper face and white lower face, with each flower petal having a darker center and markings on the upper face.
10. The flowering time is early and flowering is uniform.
11. Due to its compact growth habit, Merisweet can be treated with less growth regulator.
12. The plant does not readily form long stems but the shape of the plant stays round.
13. The foliage and the flower stalks of Merisweet are slightly hairy as a result of which the variety is not very susceptible to thrips.

Of the many commercial cultivars known to the present inventor, the most similar in comparison to Merisweet are the cultivars Duerom (PEL 181) and Epos (PEL 238). Reference is made to attached Chart A which compares certain characteristics of Merisweet to those same characteristics of Duerom and Epos.

In general comparison to Duerom, Merisweet has, among other things, markings on the upper and lower surfaces of the petals of the inflorescence. In general comparison to Epos, Merisweet has, among other things, a different flower color.

The accompanying color photographic drawings show typical flower and foliage characteristics of Merisweet, with colors being as true as possible with illustrations of this type. A scale in centimeters appears in each photo better to show dimensions.

The photo on Sheet 1 is a side view of a plant of Merisweet grown in a 10.5 cm pot approximately 8 weeks, showing the foliage, flower stalks and inflorescences. The photo on Sheet 2 is a close-up view of the upper and lower surfaces of typical leaves of Merisweet and the photo on Sheet 3 is a close-up view of the upper and lower surfaces of typical flowers of Merisweet.

In the following descriptin color references are made to The Royal Horticultural Society Colour Chart (R.H.S.) and Horticultural Colour Chart (H.C.C.). The color values were determined between 2:45 and 3:00 p.m. on Jul. 15, 1988 under 22,300 Klux light intensity at Wateringen, The Netherlands.

Classification:

*Botanical.*—A hybrid of the genus *Pelargonium zonale* cv. Merisweet.

*Commerical.*—Zonal geranium.

INFLORESCENCE

A. Umbel:

*Average diameter.*—Indoor, 122 mm.

*Average depth.*—Indoor, 91 mm.

*Peduncle length.*—Indoor, 172 mm.

*Pedicel length.*—Indoor, 33 mm.

*Pedicel color.*—Green.

B. Corolla:

*Average diameter.*—Indoor, 46 mm.

*Form.*—semi-double (7 to 9 petals).

*Color (general tonality of a distance of three meters)*-.—R.H.S. 73C, H.C.C. 530/1.

*Color (main body, upper surface).*—R.H.S. 73C, H.C.C. 530/1.

*Color (near margin upper face).*—R.H.S. 73C, H.C.C. 530/1.

*Color (lower side of petal).*—White.

Color dark spot center of upper face R.H.S. 67C which is stronger on upper petals.

*Diameter lower petals*—19 mm

*Length lower petals*—25 mm

*Diameter upper petals*—16 mm

*Length upper petals*—26 mm

*Petal shape*—Obovate

*Sepal color*—Green.

C. Bud:

*Shape.*—Elliptic.

*Color.*—Slightly lighter than corolla.

*Pedicel.*—Green.

D. Reproductive organs:

*Androecium.*—7–9 anthers.

*Gynoecium.*—4–5 stigma.

E. Spring flowering:

*Response period.*—In Wateringen, The Netherlands in 1988, 60% of plants had at least 1 flower open 13 weeks after planting unrooted cuttings.

F. Outdoor flower production: The flower count in 1989 in Wateringen, The Netherlands was between 41–46 flowers per plant from June through October observation period.

G. Durability: 100% shatter resistance.

PLANT

A. Foliage:

*Form.*—Generally round, with open base.

*Margin.*—Bicrenate.

*Color.*—Medium green (R.H.S. 138A).

*Zonation.*—light and very weak (R.H.S. 137C).

*Length.*—42 mm.

*Diameter.*—77 mm.

Tolerance of botrytis.—Good.

B. General appearance and form:

*Internode length.*—33 mm.

*Branching pattern.*—An average of 4.3 branches per plant.

*Height.*—256 mm.

*Diameter.*—256 mm.

CHART A

COMPARISON OF MERISWEET AND DUEROM AND EPOS

| Inflorescence | Merisweet | Duerom (PEL 181) | Epos (PEL 238) |
|---|---|---|---|
| color top petal surface | HCC 530/1 RHS 73C | HCC 530/2 RHS 69A | HCC 527 RHS 68C |
| markings top petal surface | present | absent | present |
| color lower petal surface | HCC 530/1 RHS 73C | HCC 530/2 | HCC 527/2 RHS 68C |
| markings lower petal surface | present | absent | present |

I claim:

1. A new and distinct cultivar of geranium plant named Merisweet, as illustrated and described.

* * * * *

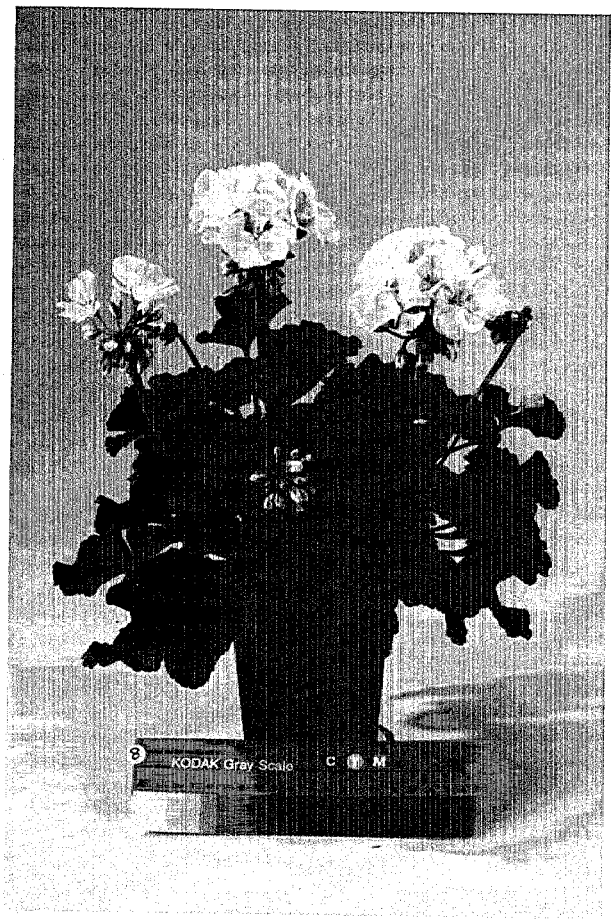
KODAK Gray Scale
C
M

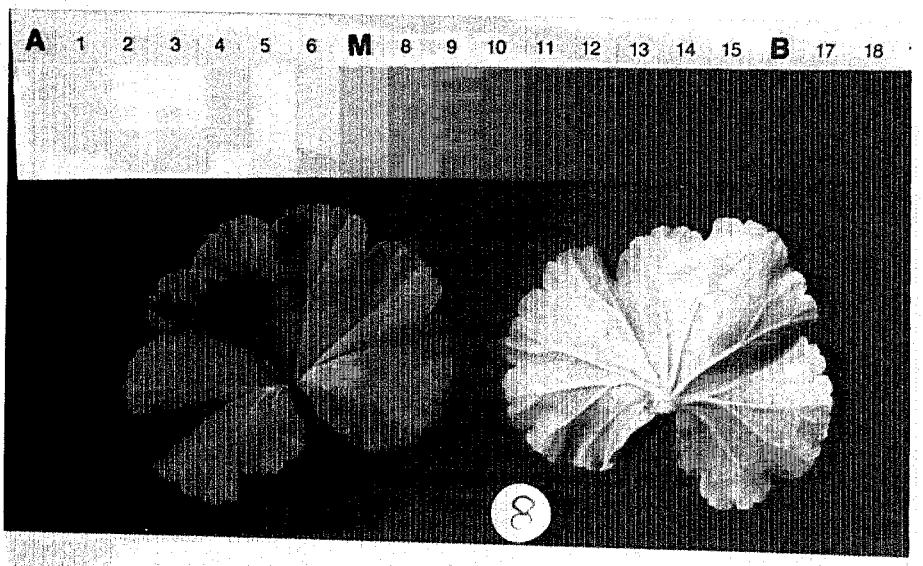
A 1 2 3 4 5 6 M 8 9 10 11 12 13 14 15 B 17 18
8

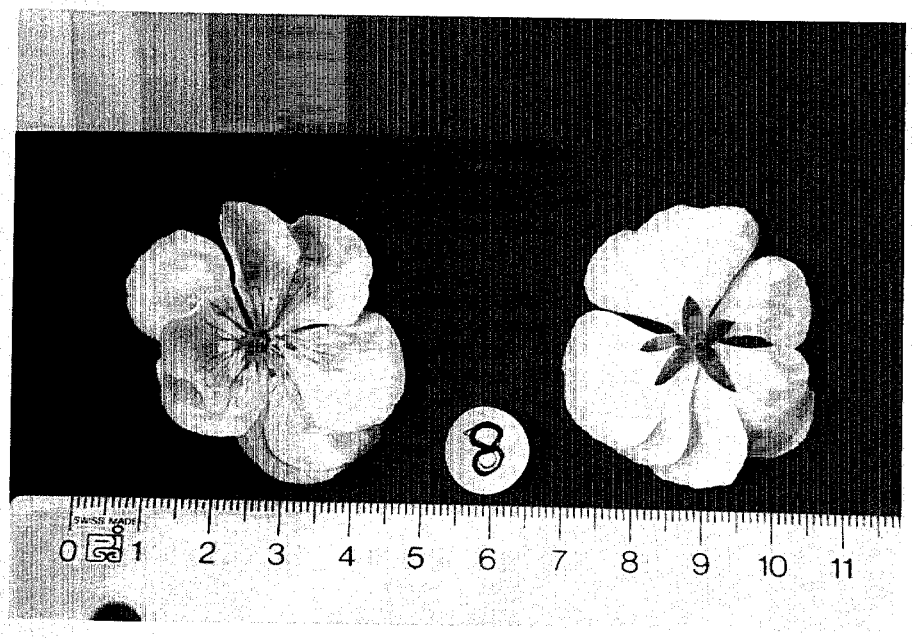
8
SWISS MADE
0 1 2 3 4 5 6 7 8 9 10 11